United States Patent [19]

Sung et al.

[11] Patent Number: 4,857,661

[45] Date of Patent: Aug. 15, 1989

[54] BICYCLIC KETO-ACIDS PREPARATION

[75] Inventors: Rodney L. Sung, Fishkill; Benjamin J. Kaufman, Hopewell Junction, both of N.Y.

[73] Assignee: Texaco Inc., White Plains, N.Y.

[21] Appl. No.: 821,713

[22] Filed: Jan. 23, 1986

[51] Int. Cl.$^4$ ............................................. C07C 51/083
[52] U.S. Cl. ..................................... 562/502; 549/300
[58] Field of Search .................... 562/502; 549/300

[56] References Cited

U.S. PATENT DOCUMENTS 4,385,904  5/1983  Sawicki et al. ..................... 44/56

Primary Examiner—Michael L. Shippen
Attorney, Agent, or Firm—Robert A. Kulason; James J. O'Loughlin; Vincent A. Mallare

[57] ABSTRACT

Alkyl substituted or unsubstituted, bicyclic keto acids may be prepared by cyclizing unsaturated, cyclic dicarboxylic acid anhydrides in the presence of a strong Bronsted acid catalyst. The products may be useful as corrosion inhibitors in alcohol fuels and as intermediates in petroleum, pharmaceutical and additive manufacture.

13 Claims, No Drawings

BICYCLIC KETO-ACIDS PREPARATION

FIELD OF THE INVENTION

This invention relates to unsaturated bicyclic keto-acids bearing pendant alkyl groups and to a method of preparing these products which as the free acids find use as corrosion inhibitors in alcohol fuels and intermediates in petroleum, pharmaceutical and additive manufacture.

RELATED CASE

The present invention is related to the invention of U.S. Pat. No. 4,385,904 issued to Sawicki et al, and directed to cyclized keto acids and their methods of preparation.

BACKGROUND OF THE INVENTION

As is well known to those skilled in the art, keto-acids may be used as soaps, in various flavor formulations, as chemical or pharmaceutical intermediates (such as in a prostaglandin synthesis), and additive manufacture. Constant attempts are being made to provide new techniques and compositions which may find use in these fields and provide improved products.

It is an object of this invention to provide a novel process for preparing bicyclic keto acids. Other objects will be apparent to those skilled in the art.

STATEMENT OF THE INVENTION

In accordance with certain of its aspects, this invention is directed to a process which comprises cyclizing an unsaturated cyclic tetrahydrophthalic dicarboxylic acid anhydride at a temperature ranging from about 25° C. to about 160° C. for a period of about 1 to about 48 hours in the presence of a strong Bronsted acid catalyst, thereby forming a bicyclic keto-acid; and recovering said bicyclic keto-acid.

DESCRIPTION OF THE INVENTION

The bicyclic keto-acid products which may be obtained from the practice of the process of this invention may be those obtained by the cyclizing of tetrahydrophthalic anhydrides of the formula:

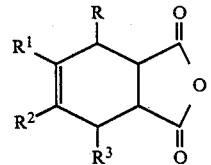

wherein R, $R^1$, $R^2$, and $R^3$ are H, $CH_3$— or $C_2H_5$—, etc.

Typical of these unsubstituted or alkyl substituted cyclic alken-3-yl-dicarboxylic acid anhydrides are (i) tetrahydrophthalic acid anhydride; (ii) 2,3,4,5,-tetramethyl tetrahydrophthalic acid anhydride; (iii) 2, 3, 4, 5-tetraethyl tetrahydrophthalic acid anhydride; etc.

Bicyclic keto-acid products may be prepared by contacting the cyclic alken-3-yl-dicarboxylic acid anhydride in an inert solvent with a strong Bronsted acid catalyst under anhydrous conditions.

The inert solvents which may be employed in the process include hydrocarbons such as benzene, toluene, xylene, etc; liquid halogenated hydrocarbons typified by methylene dichloride, chloroform, carbon tetrachloride, trichlorethane, etc; liquid nitrohydrocarbons typified by nitrobenzene, nitropropane, nitrobutane; carbon disulfide; etc. The preferred solvent is xylene.

Preferably the inert solvent is present in an amount of about 0.5 to about 10.0 parts per part of anhydride, preferably about 4.0 parts.

The catalyst (vida infra) may be present in the amount of about 0.01 parts to about 1.0 part per part of anhydride, preferably about 0.4 parts.

The reaction may be carried out by contacting the anhydride in an inert solvent with a catalytic amount of acid. Typically, the temperature at which this reaction takes place is about 25° C. to about 160° C., preferably about 60° C. to about 150° C., and more preferably about 140° C.; under atmospheric pressure.

The reaction normally may proceed with agitation over a period of about 1 to about 48 hours, preferably about 1.0 to about 12.0 hours.

After cooling, the reaction mixture is filtered and the solid residue is washed with acetone. Then, the acetone and xylene are combined and stripped under vacuum.

The product bicyclic keto acid derived mixture is prepared from a tetrahydrophthalic acid anhydride material wherein R, $R^1$, $R^2$, and $R^3$ are each H, $CH_3$— or $C_2H_5$—. Typical products are illustrated by the structures shown below in FIG. I.

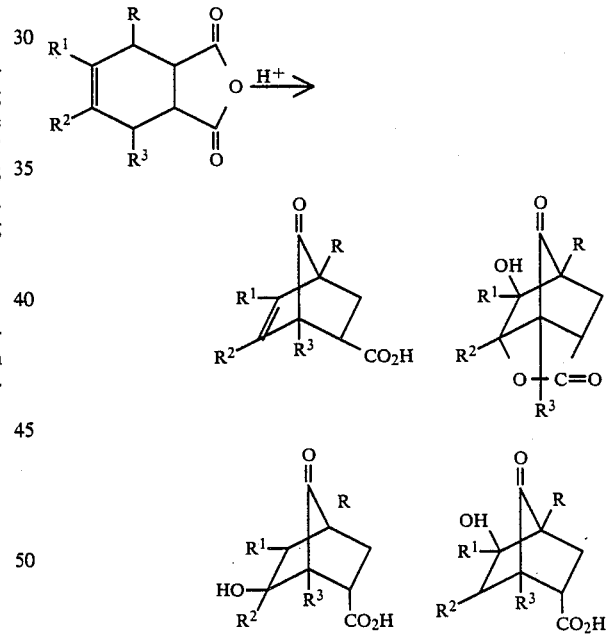

FIG. 1

Certain bicyclic keto-acids can be starting compounds for the synthesis of prostaglandins. This would be an inexpensive way for synthesizing the normally expensive starting compound.

Although it may be possible to effect separation of the several product bicyclic keto-acids as by chromatographic methods (gas or column chromatography), it is found that for many uses this is not necessary. If the product is to be further treated in accordance with this invention, satisfactory results may be attained with no further work-up or pretreating after the removal of the solvent.

In the practice of the present process, the strong Bronsted acid catalysts which may be employed may be characterized by its pKa of less than about −9 and typically about −10 to about −15.

Commercially available strong Bronsted acid which may be employed in the present process include:
(i) HClO$_4$—perchloric acid;
(ii) CF$_3$SO$_3$H—trifluoromethane sulfonic acid;
(iii) FSO$_3$H—fluorosulfonic acid; and
(iv) Nafion—H-501 resin—a perfluorosulfonic acid polymer superacid resin catalyst made by Du Pont of Wilmington, Del.

The preferred strong Bronsted acid may be one contained in an organic resin or inorganic support. This allows for easy removal from the reaction mixture as by filtration and easy recycle or regeneration. One such preferred superacid resin catalyst is the Nafion H-501 catalyst, an anhydrous acidic resin stable at temperatures above 100° C. Other suitable catalysts include the well known cross-linked styrene/divinylbenzene copolymers containing sulfonic acid groups which are preferably prepared so as to be highly porous. Such macroporous resins are well-known and may be produced, for example, according to the procedures of U.S. Pat. Nos. 3,418,262; 3,509,078; 3,551,358; 3,637,535 or 3,586,646. The preferred catalyst is the Nafion H-501 resin in its acidic form. The granulated perfluorosulfonic acid polymer has a nominal diameter of 1.0 cm and is formed by copolymerization of tetrafluoroethylene and various monomers such as perfluoro-3,6-dioxa-4-methyl-7-octene sulfonyl fluoride.

The Nafion resin is manufactured and marketed by E. I. du Pont de Nemours and Company of Wilmington, Del.

Prior to use, the resin is treated with a strong acid so as to convert the resin into the acid form. If desired, the acidity of these solid acids can be further increased by complexing with higher valency metal fluorides, such as SbF$_5$, TaF$_5$ or NbF$_3$.

The catalyst may be present in an amount of about 0.01 to about 1.0 parts, preferably about 0.4 parts per part of acid anhydride. This catalytic amount of acid is found to permit reaction to be readily carried out.

The reaction may be carried out by contacting the charge anhydride in an inert solvent in the presence of the catalytic amount of a strong Bronsted acid catalyst Typically, the temperature is about 25° C. to about 160° C., preferably about 65° C. to about 150° C., more preferably about 140° C.; at preferably atmospheric pressure. The reaction normally may proceed with agitation over about 1 to about 48 hours, preferably about 1 hour at the reflux temperature of the solvent, e.g., xylene.

Work-up of the reaction mixture may include filtration to remove the strong Bronsted acid resin catalyst (which may be readily reused repeatedly without any regeneration treatment). The solvent may then be stripped off if desired—although the reaction mixture may, if desired, be used as is i.e. product plus solvent. The Nafion resin is further washed with a polar solvent which is combined with the other solvent and stripped under vacuum.

The product keto acid derived reaction mixture may be considered to include the components shown above in FIG. I. The structure of the bicyclic material is supported by the various analytical data. Perhaps the most conclusive evidence is obtained using carbon 13 NMR spectroscopy. The technique is quite sensitive to the environment experienced by each carbon atom in the compounds in question. In the above case, the starting material contains no low field resonances below 175 PPM. By contrast, reaction with Nafion H-501 catalyst results in a complex spectra containing a new resonance at 208 PPM. This unique resonance is characteristic of a carbonyl carbon in the 7 position of a bicyclic (2.2.1) system. This data, along with the characteristic carbonyl absorbances in the IR spectrum and mass spectral data constitutes the bulk of our analytical data.

Although it may be possible to effect separation of the product bicyclic keto acids by chromatographic methods (gas or column chromatography), it is found that for many uses this is not necessary. For example, if the product is to be converted to metal salts or to quaternary amine salts for use as dispersants, detergents, friction modifiers, corrosion inhibitors, etc., satisfactory results may be attained with no further work-up or pretreating after preferred removal of the solvent.

While not limiting, the following Example is illustrative of the present invention.

EXAMPLE

Cyclization Of Tetrahydrophthalic Anhydride

To a solution of 42.7 parts of tetrahydrophthalic anhydride (Aldrich Chemical Co.) in 170 ml of xylene was added 16 parts of Nafion H-501. The mixture was then heated and stirred at about 140° C. for 1 hour with a slow stream of nitrogen passed through the solution at all times.

After cooling the solution to about 25° C., the mixture was filtered and the residue triturated with acetone. After a second filtration the acetone and xylene solutions were combined and stripped under vacuum. Based upon the analytical data discussed above, the bicyclic products shown in FIG. I were produced and identified.

We claim:

1. A process for preparing unsaturated bicyclic keto-acids, said process comprising:
   (a) cyclizing an unsaturated, unsubstituted or alkyl substituted tetrahydrophthalic acid anhydride in the presence of a strong Bronsted acid catalyst at a temperature of about 25° C. to about 160° C. for about 1 to about 48 hours, thereby forming bicyclic keto-acids; and
   (b) recovering said cyclic keto-acids.

2. The process of claim 1, wherein said acid anhydride is 2,3,4,5 - tetrahydrophthalic anhydride.

3. The process of claim 1, wherein said acid anhydride is 2, 3, 4, 5-tetramethyl tetrahydrophthalic anhydride.

4. The process of claim 1, wherein said cyclizing is carried out by contacting said acid anhydride in an inert hydrocarbon solvent in the presence of said Bronsted acid catalyst.

5. The process of claim 4, wherein said inert hydrocarbon solvent is xylene.

6. The process of claim 1, wherein said catalyst is present in the amount of about 0.01 to about 1.0 part per part of acid anhydride.

7. The process of claim 6, wherein said catalyst is present in the amount of about 0.4 parts per part of acid anhydride.

8. The process of claim 1, wherein said catalyst has a pKa of less than about −9.

9. The process of claim 1, wherein said catalyst has a pKa of about −10 to about −15.

10. The process of claim 1, wherein said catalyst is a resin catalyst.

11. The process of claim 10, wherein said resin catalyst is a perfluorosulfonic acid resin catalyst.

12. A process of preparing a bicyclic keto-acids which comprises
   (a) cyclizing an unsaturated, unsubstituted or alkyl substituted tetrahydrophthalic acid anhydride at about 25° C. to about 160° C. for about 1 to about 48 hours in an inert hydrocarbon solvent in the presence of a strong Bronsted acid resin catalyst thereby forming a reaction mixture containing a bicyclic keto-acid;
   (b) filtering said strong Bronsted acid resin catalyst from said reaction mixture; and
   (c) recovering said bicyclic keto acid.

13. The process of claim 12, wherein said cyclizing is carried out in xylene in the presence of a perfluorosulfonic acid resin catalyst at about 140° C. for about 1.0 hour.

* * * * *